United States Patent [19]
Wynn

[11] Patent Number: 5,185,531
[45] Date of Patent: Feb. 9, 1993

[54] WINDOW CLEANER FOR INLINE OPTICAL SENSORS

[75] Inventor: William H. Wynn, Hillsborough, Calif.

[73] Assignee: Wedgewood Technology, Inc., San Carlos, Calif.

[21] Appl. No.: 766,858

[22] Filed: Sep. 26, 1991

[51] Int. Cl.$^5$ .............................................. G01N 21/15
[52] U.S. Cl. ................................... 250/431; 250/573; 250/576
[58] Field of Search ........... 250/431, 428, 430, 432 R, 250/435, 573, 574, 576

[56] References Cited

U.S. PATENT DOCUMENTS

| | | | |
|---|---|---|---|
| 3,584,178 | 6/1971 | Huber et al. | 219/61.1 |
| 3,844,661 | 10/1974 | Birkett et al. | 250/576 |
| 3,953,136 | 4/1976 | Hach | 250/576 |
| 4,021,120 | 5/1977 | Muller et al. | 250/573 |
| 4,940,902 | 7/1990 | Mechalas et al. | 250/573 |

FOREIGN PATENT DOCUMENTS 2332455 1/1975 Fed. Rep. of Germany ...... 250/431

Primary Examiner—Jack I. Berman
Assistant Examiner—James Beyer
Attorney, Agent, or Firm—Flehr, Hohbach, Test, Albritton & Herbert

[57] ABSTRACT

Apparatus for cleaning the interior surface of a window in an inline optical sensors which is subject to contamination and fouling by a product stream in contact therewith. The window surface is wiped by a blade driven by a pneumatic operator, and the amount of air supplied to the operator is adjusted to control the speed at which the blade moves across the window surface. When a cleaning operation is initiated, the blade is wiped across the window surface a predetermined number of times, and measurements utilizing data from the sensor are suspended until the cleaning operation is completed and the data has had time to restabilize.

13 Claims, 2 Drawing Sheets

WINDOW CLEANER FOR INLINE OPTICAL SENSORS

BACKGROUND OF THE INVENTION

1. Field of the Invention

This invention pertains generally to inline optical sensors for obtaining data from a fluid product stream and, more particularly, to apparatus for cleaning optical windows in such sensors.

2. Related art

Inline measurement sensors such as spectrophotometers, colorimeters, turbidimeters, refractometers, ultrasonic flow and particle sensing devices, and the like, have optical windows through which measurements are made on fluid product streams. To have reliable measurements, it is important that the window surfaces remain clean and free of films, dirt or other contamination. Unfortunately, since the windows are in contact with the product streams, they are susceptible to contamination and fouling thereby. This contamination can introduce errors into a measurement or even prevent the measurement from being made.

Measurements such as low turbidity are particularly susceptible to fouling of window surfaces by the product stream. This fouling results in the scattering of the light beam and is seen by the detector as suspended solids in the product stream. In low level measurements, e.g. 5.0 ppm or less, the scattering due to window fouling can exceed the scattering produced by the suspended solids. Examples of low level turbidity measurements where potential window fouling is high include measurements of oil in water, suspended solids in potable water and waste treatment effluents.

Heretofore, there have been attempts to clean the windows of inline optical sensors by techniques such as purging with water and/or another liquid, ultrasonic cleaning, and the application of protective coverings. None of the techniques, however, has provided a consistent and controllable cleaning of the critical optical surfaces.

It is in general an object of the invention to provide a new and improved apparatus for cleaning windows of inline optical sensors which come into contact with product streams.

Another object of the invention is to provide a window cleaner of the above character which overcomes the limitations and disadvantages of the techniques heretofore employed for cleaning the windows of inline sensors.

SUMMARY OF THE INVENTION

These and other objects are achieved in accordance with the invention by providing a window cleaner with a blade for mechanically wiping the interior surface of a window in an inline optical sensor. The blade is driven by a pneumatic operator, and the amount of air supplied to the operator is adjusted to control the speed at which the blade moves across the window surface. When a cleaning operation is initiated, the blade is wiped across the window surface a predetermined number of times, and measurements utilizing data from the sensor are suspended until the cleaning operation is completed and the data has had time to restabilize.

DETAILED DESCRIPTION

Figure 2:
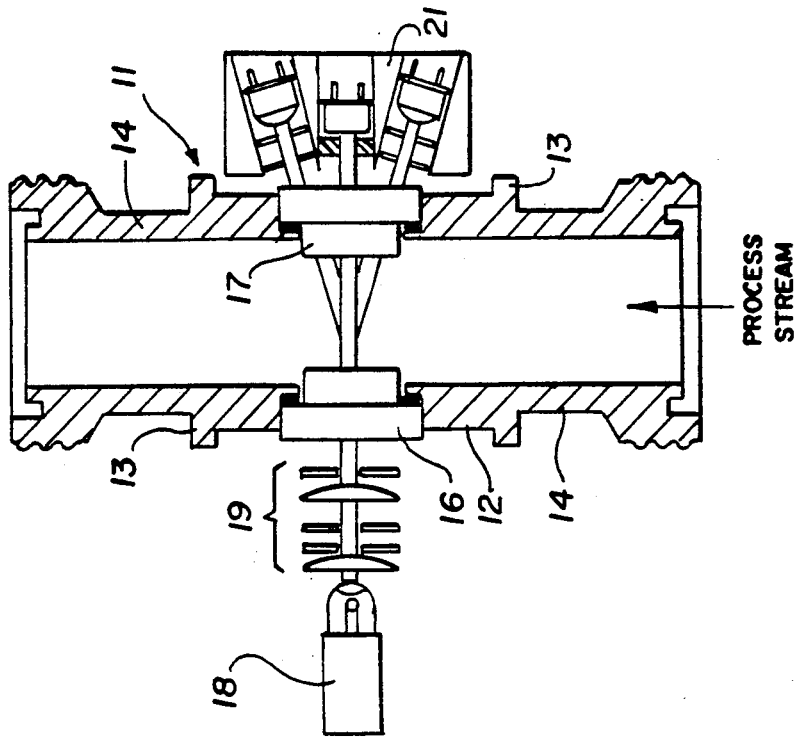
FIG. 2 is a cross-sectional view, somewhat schematic, of the inline optical sensor in the embodiment of FIG. 1.
Figure 1:
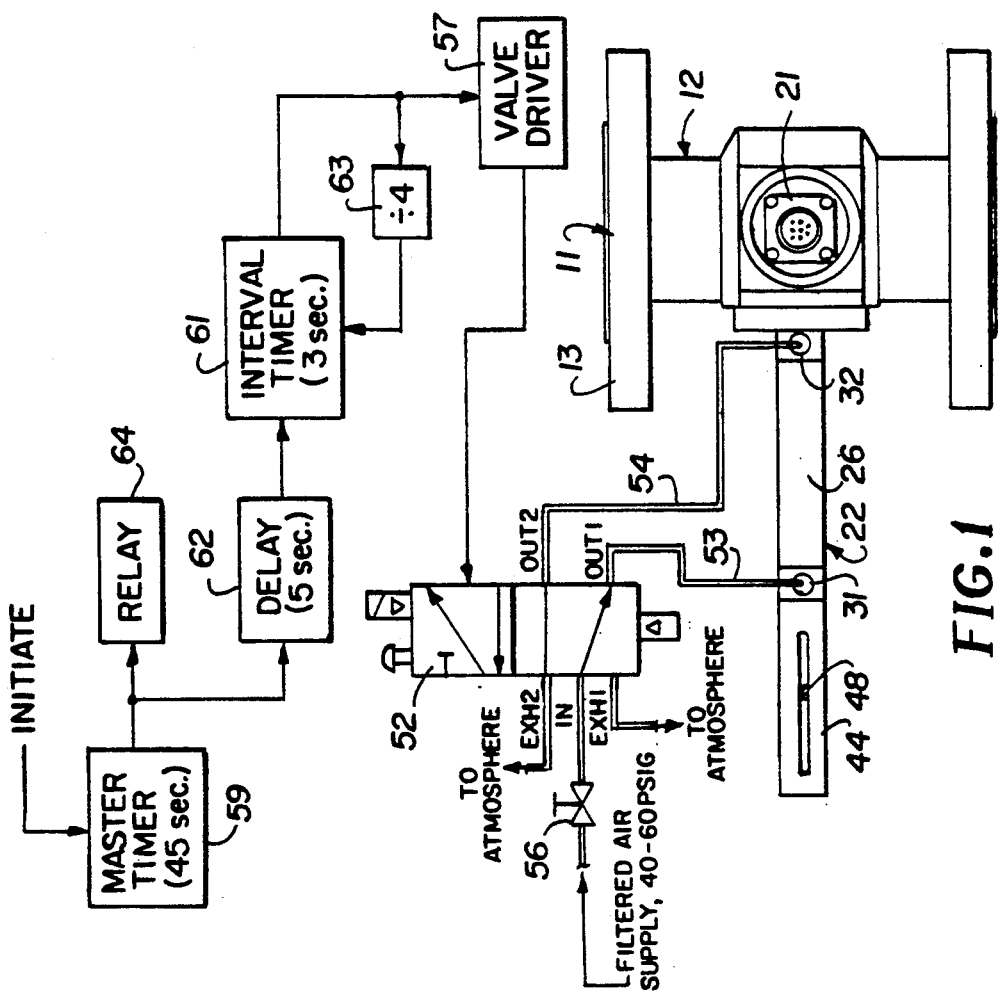
FIG. 1 is a schematic diagram of one embodiment of a window cleaner according to the invention installed on an inline optical sensor.
Figure 3:
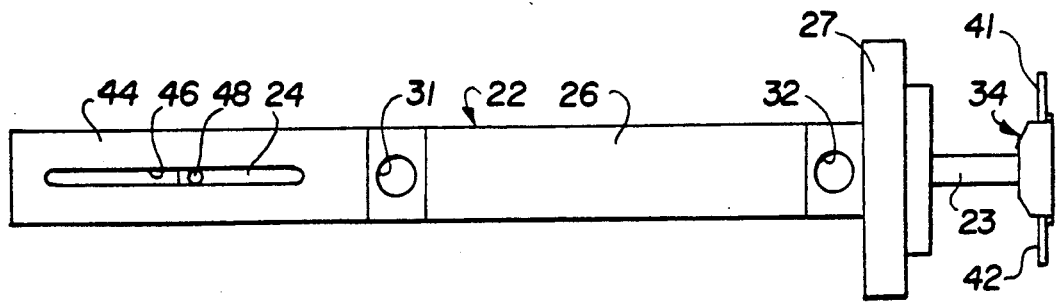
FIG. 3 is a side elevational view of the pneumatic operator and wiper blade assembly in the embodiment of FIG. 1.
Figure 5:
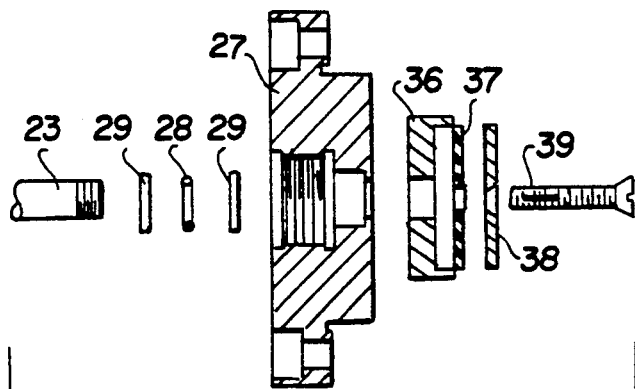
FIG. 5 is an exploded cross-sectional view of the wiper blade assembly in the embodiment of FIG. 3, with the assembly being rotated 90° from the position in which it is shown in FIG. 3.
Figure 4:
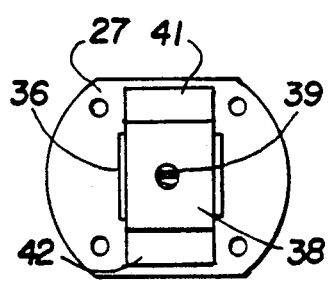
FIG. 4 is an end view of the operator and blade assembly of FIG. 3.
Figure 6:
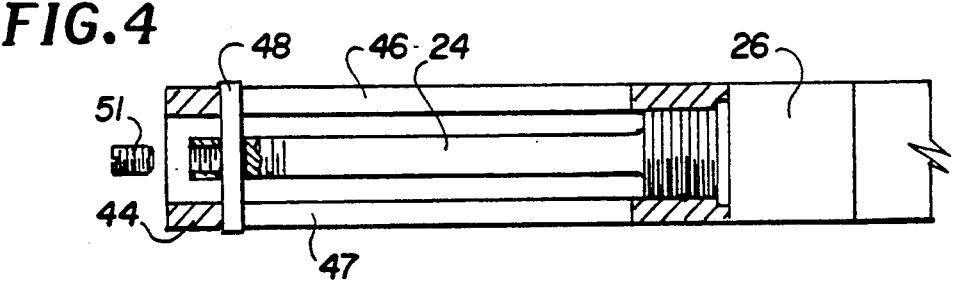
FIG. 6 is a fragmentary cross-sectional view of an anti-rotation assembly in the operator and wiper blade assembly of FIG. 3.

In the drawings, the window cleaner is illustrated in connection with an inline optical sensor 11 such as a colorimeter, a spectrophotometer, a turbidimeter, a refractometer, a fluorimeter, or the like. The sensor has a housing 12 with flanges 13 for connection to the piping 14 which carries the stream of product to be monitored. Optically transparent entrance and exit windows 16, 17 are provided in the housing on opposite sides of the product stream. A light source 18 and projection optics 19 are positioned outside the entrance window for directing a beam of light through the product stream, and a sensor assembly 21 is positioned outside the exit window for receiving the light passing through the product stream and providing electrical signals corresponding thereto. The data represented by these signals is applied to suitable monitoring and/or recording equipment to provide information about the product stream.

An operating cylinder 22 is mounted on a side of the housing between the entrance and exit windows. In the embodiment illustrated, the cylinder is a double acting pneumatic cylinder with output shafts 23, 24 movable between advanced and retracted positions relative to the body 26 of the cylinder. One end of the body is threaded into an adaptor 27 which is fitted into a port in the sensor housing with output shaft 23 extending between windows 16, 17 in a direction generally parallel to the inner surfaces of the windows and perpendicular to the axis of the projection optics. A fluid-tight seal is provided between the shaft and the adapter by an o-ring 28 and back-up rings 29. The adapter is secured to the housing by mounting screws (not shown), with an o-ring gasket (not shown) providing a fluid-tight seal between the adapter and the housing. The cylinder has inlet ports 31, 32 through which pressurized air is applied to move output shafts 23, 24 between their extended and retracted positions. The shafts are connected rigidly together, with shaft 23 moving toward its extended position when air is applied to inlet port 31 and shaft 24 moving toward its extended position when air is applied to inlet port 32.

Figure 7:
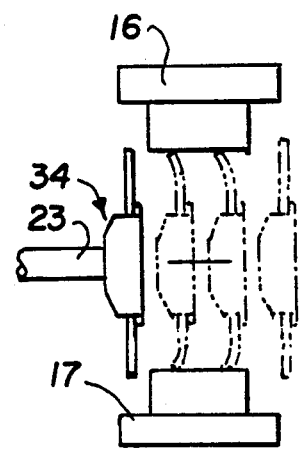
FIGS. 7 and 8 are operational views of wiper blades in the embodiment of FIG. 3.
Figure 8:
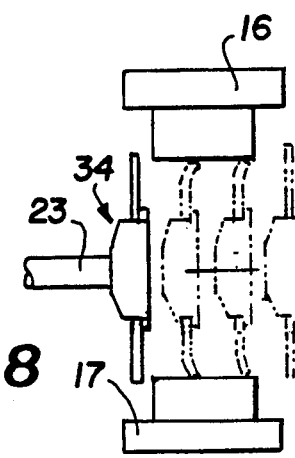

A wiper blade assembly 34 is mounted on the end of output shaft 23 inside the sensor cell. This assembly includes a blade holder or base 36, a wiper blade 37, and a retaining plate 38. The blade holder or base is threaded onto the end of the output shaft, and the retaining plate and blade are clamped to the holder by a screw 39 which is threaded into the end of the shaft. The wiper blade is generally rectangular, with the end portions of the blade extending beyond the side edges of the holder and retaining plate to form separate wipers or blades 41, 42 for engagement with the surfaces of the two windows. The blade is fabricated of a flexible material such as nitrile rubber which is compatible with the fluid in the process stream. The length of the blades is somewhat greater than the distance between the surfaces, and as illustrated in FIGS. 7-8, the tips of the blades flex in opposite directions to provide a wiping or squeegeeing action as the shaft is extended and retracted.

The blade assembly is smaller than the port in the sensor housing in which adapter 27 is mounted, which permits the window cleaner to be readily installed on and removed from the sensor housing, e.g. for cleaning or replacement of the wiper blades.

Means is provided for preventing rotation of output shaft 23 and keeping the edges of blades 41, 42 in parallel alignment with the window surfaces. This means comprises a cylinder 44 which is threaded onto the end of the operating cylinder body 26 opposite adapter 27, with output shaft 24 extending coaxially within cylinder 44. Longitudinally extending slots 46, 47 are formed on opposite sides of cylinder 44, and a guide pin 48 affixed to shaft 24 is received in these slots to constrain the two output shafts against rotation while permitting them to move back and forth between their extended and retracted positions. The guide pin passes through a crossbore 49 in shaft 24 and is secured there by a setscrew 51.

The delivery of pressurized air to cylinder 22 is controlled by a solenoid operated, two position valve 52, with air lines 53, 54 connected between the outlet ports of the valve and the inlet ports of the cylinder.

Air is supplied to the valve at a pressure on the order of 40-60 psi from a suitable source through a flow restricting valve 56 by which the volume of air supplied to the cylinder is adjusted. This controls the speed of the cylinder strokes and, hence, the speed at which the wiper blades move across the window surfaces. Operating power is applied to the solenoid in the valve by a valve driver 57.

A control system 58 is connected to the valve driver to control the operation of the cleaner. This system causes the cylinder to operate for a predetermined number of strokes each time it is actuated, and it also suspends operation of the monitoring and/or recording equipment until the cleaning cycle is completed and the data from the sensors has had time to stabilize again.

The control system includes a master timer 59 to which signals are applied to initiate a cleaning operation or cycle. These signals can come from any suitable source such as a manually operated pushbutton switch or a program which causes the windows to be cleaned at periodic intervals or when a need to clean them is detected. The master timer sets the length of the cleaning cycle for a suitable period, such as 45 seconds.

The signal from master timer 59 is applied to an interval timer 61 through a delay circuit 62. The interval timer has a 50% percent duty cycle and delivers output pulses of suitable duration, e.g. 3 seconds on and 3 seconds off. These pulses are applied to the valve driver to control the application of the pressurized air to the operating cylinder. The output pulses are counted by a binary counter 63 which turns the interval timer off at a count of four.

The output signal from the master timer is also applied to a relay 61 to operate a set of switch contacts to interrupt the use of data from the sensor during the cleaning operation and while the data stabilizes thereafter. With a 45 second master timer, 5 second delay in the actuation of the interval timer, and 4 double strokes of the operating cylinder with 6 seconds between each, the data has approximately 16 seconds in which to stabilize following the wiping of the windows.

The invention has a number of important features and advantages. It is simple in operation and provides a positive cleaning action. It enables low level measurements of color, turbidity, solids, refraction and the like to be made in process streams that foul or contaminate the viewing windows of a sensor. It is readily adapted to different line sizes and connectors, and can be used in a variety of applications such as oil field facilities, waste treatment facilities and potable water plants. The wiper blades can be selected for compatibility with any desired application, and the cleaning operation can be initiated by the user on any desired time cycle. Wiper speed can be adjusted to maximize the wiping action and blade life, and the blades cannot be rotated out of proper alignment by the product stream. The system allows full flow sensor measurement.

It is apparent from the foregoing that a new and improved window cleaner for inline optical sensors has been provided. While only certain presently preferred embodiments have been described in detail, as will be apparent to those familiar with the art, certain changes and modifications can be made without departing from the scope of the invention as defined by the following claims.

What is claimed is:

1. In apparatus for monitoring a product stream: an inline optical sensor having a housing with optically transparent generally planar windows on opposite sides thereof, means for continuously passing a fluid product stream through the sensor in contact with sufaces of the windows, means for optically monitoring the entire product stream through the windows to provide data about the product stream, an operator mounted on the housing between the sides on which the windows are located and having an output shaft movable axially between advanced and retracted positions in a direction generally parallel to the window surfaces, and a wiper blade connected to the shaft for wiping engagement with the window surfaces as the shaft moves between the advanced and retracted positions.

2. The apparatus of claim 1 wherein the operator comprises a double acting pneumatic cylinder.

3. The apparatus of claim 2 including means connected to the pneumatic cylinder for preventing rotation of the shaft as it moves between the advanced and retracted positions.

4. The apparatus of claim 2 including means for adjusting the amount of air supplied to the cylinder to control the speed at which the wiper moves across the window surface.

5. The apparatus of claim 1 including means connected to the operator for conditioning the operator to move the shaft between the advanced and retracted positions a predetermined number of times when a cleaning operation is initiated.

6. The apparatus of claim 5 including means responsive to initiation of a cleaning operation for suspending measurements utilizing data from the sensor during the cleaning operation.

7. In apparatus for monitoring a product stream: an optical sensor cell having interior window surfaces on opposite sides thereof, means for passing a product stream through the cell in contact with the window surfaces, a pneumatic operator mounted on the outside of the cell with an output shaft extending into the cell between the window surfaces for movement between axially advanced and retracted positions in a direction generally parallel to said surfaces, a blade holder mounted on the shaft between the windows, flexible wiper blades extending from opposite sides of the blade holder for wiping engagement with the window surfaces, an air source, an electrically operated valve connected between the air source and the operator, means for applying electrical pulses to the valve to actuate the valve to apply air to the operator to move the shaft between the advanced and retracted positions and thereby wipe the blades across the window surfaces in response to the pulses, means for counting the number of pulses applied to the valve, and means for discontinuing the application of pulses to the valve when the count reaches a predetermined number.

8. The apparatus of claim 7 including means for adjusting the amount of air supplied to the operator to control the rate at which the blades wipe across the window surfaces.

9. The apparatus of claim 7 including means connected to the operator externally of the cell for preventing rotation of the shaft as it moves between the advanced and retracted positions.

10. In apparatus for monitoring a product stream: an optical sensor cell having an optically transparent window, means for optically monitoring a product stream through the window and providing data about the product stream, means for feeding a product stream through the cell in contact with a surface of the window, an operator having an output shaft movable between advanced and retracted positions in a direction generally parallel to the window surface, a wiper blade connected to the shaft for wiping engagement with the window surface as the shaft moves between the advanced and retracted positions, a controller responsive to a starting command for actuating the operator to wipe the blade across the window surface for a predetermined period of time following receipt of the command, and means for inhibiting measurements with the data from the sensor cell during the time the window surface is being wiped.

11. The apparatus of claim 10 wherein the controller includes means for applying pulses to the operator to actuate the same, means for counting the pulses, and means for discontinuing the application of pulses when the number of pulses counted reaches a predetermined number.

12. The apparatus of claim 10 wherein the means for inhibiting measurements includes a timer responsive to the starting command for generating a signal defining an interval of time greater than the predetermined period, and controlled switching means responsive to the timer signal for inhibiting measurements with the data during the interval.

13. The apparatus of claim 10 wherein the operator comprises a pneumatic cylinder.

* * * * *